US010179236B2

United States Patent
Haasl et al.

(10) Patent No.: US 10,179,236 B2
(45) Date of Patent: Jan. 15, 2019

(54) LEADLESS CARDIAC PACING DEVICES

(71) Applicant: Cardiac Pacemakers, Inc., St. Paul, MN (US)

(72) Inventors: Benjamin J. Haasl, Forest Lake, MN (US); Dana Sachs, Pine City, MN (US); Keith R. Maile, New Brighton, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 804 days.

(21) Appl. No.: 14/452,680

(22) Filed: Aug. 6, 2014

(65) Prior Publication Data

US 2015/0051616 A1 Feb. 19, 2015

Related U.S. Application Data

(60) Provisional application No. 61/866,799, filed on Aug. 16, 2013.

(51) Int. Cl.
*A61B 19/00* (2006.01)
*A61N 1/05* (2006.01)
(Continued)

(52) U.S. Cl.
CPC .......... *A61N 1/0573* (2013.01); *A61N 1/3756* (2013.01); *A61N 1/37205* (2013.01);
(Continued)

(58) Field of Classification Search
CPC .. A61N 1/0573; A61N 1/362; A61N 1/37205; A61N 1/3756; A61N 1/375;
(Continued)

(56) References Cited

U.S. PATENT DOCUMENTS 721,869 A 3/1903 Dunning
3,717,151 A 2/1973 Collett
(Continued)

FOREIGN PATENT DOCUMENTS

CA 1003904 A1 1/1977
DE 2053919 A1 5/1972
(Continued)

OTHER PUBLICATIONS

Merriam-Webster Definition of "Compound Curve", accessed on Apr. 25, 2017, <https://www.merriam-webster.com/dictionary/compound%20curve>.*
(Continued)

*Primary Examiner* — Elizabeth Houston
*Assistant Examiner* — Mohamed Gabr
(74) *Attorney, Agent, or Firm* — Seager, Tufte & Wickhem LLP

(57) ABSTRACT

Implantable leadless pacing devices and medical device systems including an implantable leadless pacing device are disclosed. An example implantable leadless pacing device may include a pacing capsule. The pacing capsule may include a housing. The housing may have a proximal region and a distal region. A first electrode may be disposed along the distal region. One or more anchoring members may be coupled to the distal region. The anchoring members may each include a region with a compound curve.

19 Claims, 7 Drawing Sheets

(51) Int. Cl.
*A61N 1/375* (2006.01)
*A61N 1/372* (2006.01)
*A61N 1/362* (2006.01)

(52) U.S. Cl.
CPC ........ *A61N 1/362* (2013.01); *A61N 2001/058* (2013.01); *A61N 2001/0578* (2013.01)

(58) Field of Classification Search
CPC ........ A61N 1/0587; A61N 1/057; A61N 1/05; A61N 1/059; A61N 1/0558; A61N 2001/0578; A61N 2001/058; A61B 17/3468; A61B 5/6882; A61B 5/6839; A61B 5/6869
See application file for complete search history.

(56) References Cited

U.S. PATENT DOCUMENTS

| | | |
|---|---|---|
| 3,754,555 A | 8/1973 | Schmitt |
| 3,814,104 A | 6/1974 | Irnich et al. |
| 3,835,864 A | 9/1974 | Rasor et al. |
| 3,902,501 A | 9/1975 | Citron |
| 3,943,936 A | 3/1976 | Rasor |
| 3,971,364 A | 7/1976 | Fletcher et al. |
| 3,976,082 A | 8/1976 | Schmitt |
| 4,103,690 A | 8/1978 | Harris |
| 4,112,952 A | 9/1978 | Thomas et al. |
| 4,269,198 A | 5/1981 | Stokes |
| 4,280,512 A | 7/1981 | Karr |
| 4,301,815 A | 11/1981 | Doring |
| 4,402,328 A | 9/1983 | Doring |
| 4,409,994 A | 10/1983 | Doring |
| 4,502,492 A | 3/1985 | Bornzin |
| 4,662,382 A | 5/1987 | Sluetz et al. |
| 4,898,577 A | 2/1990 | Badger et al. |
| 4,913,164 A | 4/1990 | Greene et al. |
| 5,003,990 A | 4/1991 | Osypka |
| 5,057,114 A | 10/1991 | Wittich et al. |
| 5,129,749 A | 7/1992 | Sato |
| 5,171,233 A | 12/1992 | Amplatz et al. |
| 5,193,540 A | 3/1993 | Schulman et al. |
| 5,257,634 A | 11/1993 | Kroll |
| 5,282,845 A | 2/1994 | Bush et al. |
| 5,300,107 A | 4/1994 | Stokes et al. |
| 5,318,528 A | 6/1994 | Heaven et al. |
| 5,336,253 A | 8/1994 | Gordon et al. |
| 5,405,367 A | 4/1995 | Schulman et al. |
| 5,405,374 A | 4/1995 | Stein |
| 5,411,535 A | 5/1995 | Fujii et al. |
| 5,425,756 A | 6/1995 | Heil et al. |
| 5,443,492 A | 8/1995 | Stokes et al. |
| 5,492,119 A | 2/1996 | Abrams |
| 5,522,875 A | 6/1996 | Gates et al. |
| 5,522,876 A | 6/1996 | Rusink |
| 5,545,201 A | 8/1996 | Helland et al. |
| 5,545,206 A | 8/1996 | Carson |
| 5,562,723 A | 10/1996 | Rugland et al. |
| 5,575,814 A | 11/1996 | Giele et al. |
| 5,578,068 A | 11/1996 | Laske et al. |
| 5,697,936 A | 12/1997 | Shipko et al. |
| 5,716,390 A | 2/1998 | Li |
| 5,716,391 A | 2/1998 | Grandjean |
| 5,755,764 A | 5/1998 | Schroeppel |
| 5,776,178 A | 7/1998 | Pohndorf et al. |
| 5,807,399 A | 9/1998 | Laske et al. |
| 5,837,006 A | 11/1998 | Ocel et al. |
| 5,837,007 A | 11/1998 | Altman et al. |
| 5,851,226 A | 12/1998 | Skubitz et al. |
| 5,871,531 A | 2/1999 | Struble |
| 5,908,381 A | 6/1999 | Aznoian et al. |
| 5,908,447 A | 6/1999 | Schroeppel et al. |
| 6,041,258 A | 3/2000 | Cigaina et al. |
| 6,055,457 A | 4/2000 | Bonner |
| 6,074,401 A | 6/2000 | Gardnier et al. |
| 6,078,840 A | 6/2000 | Stokes |
| 6,093,177 A | 7/2000 | Javier et al. |
| 6,129,749 A | 10/2000 | Bartig et al. |
| 6,132,456 A | 10/2000 | Sommer et al. |
| 6,181,973 B1 | 1/2001 | Ceron et al. |
| 6,188,932 B1 | 2/2001 | Lindegren |
| 6,240,322 B1 | 5/2001 | Peterfeso et al. |
| 6,251,104 B1 | 6/2001 | Kesten et al. |
| 6,290,719 B1 | 9/2001 | Garberoglio |
| 6,321,124 B1 | 11/2001 | Cigaina |
| 6,322,548 B1 | 11/2001 | Payne et al. |
| RE37,463 E | 12/2001 | Altman |
| 6,358,256 B1 | 3/2002 | Reinhardt |
| 6,363,938 B2 | 4/2002 | Saadat et al. |
| 6,381,495 B1 | 4/2002 | Jenkins |
| 6,381,500 B1 | 4/2002 | Fischer, Sr. |
| 6,408,214 B1 | 6/2002 | Williams et al. |
| 6,458,145 B1 | 10/2002 | Ravenscroft et al. |
| 6,477,423 B1 | 11/2002 | Jenkins |
| 6,500,182 B2 | 12/2002 | Foster |
| 6,510,332 B1 | 1/2003 | Greenstein |
| 6,510,345 B1 | 1/2003 | Van Bentem |
| 6,522,915 B1 | 2/2003 | Ceballos et al. |
| 6,572,587 B2 | 6/2003 | Lerman et al. |
| 6,582,441 B1 | 6/2003 | He et al. |
| 6,592,581 B2 | 7/2003 | Bowe |
| 6,623,518 B2 | 9/2003 | Thompson et al. |
| 6,626,915 B2 | 9/2003 | Leveillee |
| 6,638,268 B2 | 10/2003 | Niazi |
| 6,684,109 B1 | 1/2004 | Osypka |
| 6,711,443 B2 | 3/2004 | Osypka |
| 6,743,240 B2 | 6/2004 | Smith et al. |
| 6,755,812 B2 | 6/2004 | Peterson et al. |
| 6,909,920 B2 | 6/2005 | Lokhoff et al. |
| 6,944,507 B2 | 9/2005 | Froberg et al. |
| 6,953,454 B2 | 10/2005 | Peterson et al. |
| 7,027,876 B2 | 4/2006 | Casavant et al. |
| 7,082,335 B2 | 7/2006 | Klein et al. |
| 7,085,606 B2 | 8/2006 | Flach et al. |
| 7,092,765 B2 | 8/2006 | Geske et al. |
| 7,092,766 B1 | 8/2006 | Salys et al. |
| 7,120,504 B2 | 10/2006 | Osypka |
| 7,149,587 B2 | 12/2006 | Wardle et al. |
| 7,158,838 B2 | 1/2007 | Seifert et al. |
| 7,162,310 B2 | 1/2007 | Doan |
| 7,181,288 B1 | 2/2007 | Rezai et al. |
| 7,187,982 B2 | 3/2007 | Seifert et al. |
| 7,200,437 B1 | 4/2007 | Nabutovsky et al. |
| 7,212,869 B2 | 5/2007 | Wahlstrom et al. |
| 7,229,415 B2 | 6/2007 | Schwartz |
| 7,251,532 B2 | 7/2007 | Hess et al. |
| 7,289,853 B1 | 10/2007 | Campbell et al. |
| 7,313,445 B2 | 12/2007 | McVenes et al. |
| 7,326,231 B2 | 2/2008 | Phillips et al. |
| 7,328,071 B1 | 2/2008 | Stehr et al. |
| 7,383,091 B1 | 6/2008 | Chitre et al. |
| 7,450,999 B1 | 11/2008 | Karicherla et al. |
| 7,462,184 B2 | 12/2008 | Worley et al. |
| 7,463,933 B2 | 12/2008 | Wahlstrom et al. |
| 7,499,758 B2 | 3/2009 | Cates et al. |
| 7,509,169 B2 | 3/2009 | Eigler et al. |
| 7,515,971 B1 | 4/2009 | Doan |
| 7,532,939 B2 | 5/2009 | Sommer et al. |
| 7,558,631 B2 | 7/2009 | Cowan et al. |
| 7,634,319 B2 | 12/2009 | Schneider et al. |
| 7,647,109 B2 | 1/2010 | Hastings et al. |
| 7,657,325 B2 | 2/2010 | Williams |
| 7,678,128 B2 | 3/2010 | Boyle et al. |
| 7,717,899 B2 | 5/2010 | Bowe et al. |
| 7,731,655 B2 | 6/2010 | Smith et al. |
| 7,734,343 B2 | 6/2010 | Ransbury et al. |
| 7,740,640 B2 | 6/2010 | Ginn |
| 7,785,264 B2 | 8/2010 | Hettrick et al. |
| 7,799,037 B1 | 9/2010 | He et al. |
| 7,801,624 B1 | 9/2010 | Flannery et al. |
| 7,835,801 B1 | 11/2010 | Sundararajan et al. |
| 7,840,281 B2 | 11/2010 | Kveen et al. |
| 7,840,283 B1 | 11/2010 | Bush et al. |
| 7,860,580 B2 | 12/2010 | Falk et al. |
| 7,875,049 B2 | 1/2011 | Eversull et al. |

(56) References Cited

U.S. PATENT DOCUMENTS

| | | |
|---|---|---|
| 7,890,186 B2 | 2/2011 | Wardle et al. |
| 7,904,179 B2 | 3/2011 | Rutten et al. |
| 7,920,928 B1 | 4/2011 | Yang et al. |
| 7,993,351 B2 | 8/2011 | Worley et al. |
| 8,010,209 B2 | 8/2011 | Jacobson |
| 8,036,757 B2 | 10/2011 | Worley |
| 8,057,486 B2 | 11/2011 | Hansen |
| 8,082,035 B2 | 12/2011 | Glukhovsky |
| 8,103,361 B2 | 1/2012 | Moser |
| 8,108,054 B2 | 1/2012 | Helland |
| 8,142,347 B2 | 3/2012 | Griego et al. |
| 8,160,722 B2 | 4/2012 | Rutten et al. |
| 8,170,690 B2 | 5/2012 | Morgan et al. |
| 8,185,213 B2 | 5/2012 | Kveen et al. |
| 8,219,213 B2 | 7/2012 | Sommer et al. |
| 8,233,994 B2 | 7/2012 | Sommer et al. |
| 8,252,019 B2 | 8/2012 | Fleming, III |
| 8,295,939 B2 | 10/2012 | Jacobson |
| 8,313,445 B2 | 11/2012 | Mishima et al. |
| 8,352,025 B2 | 1/2013 | Jacobson |
| 8,352,028 B2 | 1/2013 | Wenger |
| 8,364,277 B2 | 1/2013 | Glukhovsky |
| 8,364,280 B2 | 1/2013 | Marnfeldt et al. |
| 8,406,900 B2 | 3/2013 | Barlov et al. |
| 8,406,901 B2 | 3/2013 | Starkebaum et al. |
| 8,428,750 B2 | 4/2013 | Kolberg |
| 8,452,420 B2 | 5/2013 | Flach et al. |
| 8,478,431 B2 | 7/2013 | Griswold et al. |
| 8,489,189 B2 | 7/2013 | Tronnes |
| 8,494,650 B2 | 7/2013 | Glukhovsky et al. |
| 8,504,156 B2 | 8/2013 | Bonner et al. |
| 8,518,060 B2 | 8/2013 | Jelich et al. |
| 8,527,068 B2 | 9/2013 | Ostroff |
| 8,532,790 B2 | 9/2013 | Griswold |
| 8,548,605 B2 | 10/2013 | Ollivier |
| 8,565,897 B2 | 10/2013 | Regnier et al. |
| 8,615,310 B2 | 12/2013 | Khairkhahan et al. |
| 8,634,912 B2 | 1/2014 | Bornzin et al. |
| 8,670,842 B1 | 3/2014 | Bornzin et al. |
| 8,700,181 B2 | 4/2014 | Bornzin et al. |
| 8,721,587 B2 | 5/2014 | Berthiaume et al. |
| 8,727,996 B2 | 5/2014 | Allan et al. |
| 8,738,147 B2 | 5/2014 | Hastings et al. |
| 8,758,365 B2 | 6/2014 | Bonner et al. |
| 2002/0077556 A1 | 6/2002 | Schwartz |
| 2003/0004537 A1 | 1/2003 | Boyle et al. |
| 2004/0176797 A1 | 9/2004 | Opolski |
| 2004/0230280 A1* | 11/2004 | Cates ............ A61B 17/320068 607/126 |
| 2004/0249417 A1 | 12/2004 | Ransbury et al. |
| 2005/0090890 A1 | 4/2005 | Wu et al. |
| 2005/0267555 A1 | 12/2005 | Marnfeldt et al. |
| 2006/0085039 A1 | 4/2006 | Hastings et al. |
| 2006/0247753 A1 | 11/2006 | Wenger et al. |
| 2007/0135883 A1 | 6/2007 | Drasler et al. |
| 2007/0150037 A1 | 6/2007 | Hastings et al. |
| 2007/0150038 A1 | 6/2007 | Hastings et al. |
| 2007/0233218 A1 | 10/2007 | Kolberg |
| 2007/0239248 A1 | 10/2007 | Hastings et al. |
| 2007/0255376 A1 | 11/2007 | Michels et al. |
| 2007/0276444 A1 | 11/2007 | Gelbart |
| 2007/0293904 A1 | 12/2007 | Gelbart |
| 2008/0021532 A1 | 1/2008 | Kveen et al. |
| 2008/0051863 A1* | 2/2008 | Schneider ........ A61B 17/0057 607/126 |
| 2009/0082827 A1 | 3/2009 | Kveen et al. |
| 2009/0082828 A1 | 3/2009 | Ostroff |
| 2009/0204170 A1 | 8/2009 | Hastings et al. |
| 2009/0281605 A1 | 11/2009 | Marnfeldt et al. |
| 2010/0198288 A1 | 8/2010 | Ostroff |
| 2010/0211149 A1 | 8/2010 | Morgan et al. |
| 2011/0034939 A1 | 2/2011 | Kveen et al. |
| 2011/0054555 A1 | 3/2011 | Williams et al. |
| 2011/0112548 A1 | 5/2011 | Fifer et al. |
| 2011/0125163 A1 | 5/2011 | Rutten et al. |
| 2011/0190785 A1 | 8/2011 | Gerber et al. |
| 2011/0190786 A1 | 8/2011 | Gerber et al. |
| 2011/0208260 A1 | 8/2011 | Jacobson |
| 2011/0237967 A1 | 9/2011 | Moore et al. |
| 2011/0270339 A1 | 11/2011 | Murray, III et al. |
| 2011/0270340 A1 | 11/2011 | Pellegrini et al. |
| 2011/0282423 A1 | 11/2011 | Jacobson |
| 2011/0307043 A1 | 12/2011 | Ollivier |
| 2012/0078322 A1 | 3/2012 | Dal Molin et al. |
| 2012/0078336 A1 | 3/2012 | Helland |
| 2012/0095539 A1 | 4/2012 | Khairkhahan et al. |
| 2012/0109002 A1 | 5/2012 | Mothilal et al. |
| 2012/0109079 A1 | 5/2012 | Asleson et al. |
| 2012/0109148 A1 | 5/2012 | Bonner et al. |
| 2012/0109149 A1 | 5/2012 | Bonner et al. |
| 2012/0116489 A1 | 5/2012 | Khairkhahan et al. |
| 2012/0158111 A1 | 6/2012 | Khairkhahan et al. |
| 2012/0165827 A1 | 6/2012 | Khairkhahan et al. |
| 2012/0172690 A1 | 7/2012 | Anderson et al. |
| 2012/0172891 A1 | 7/2012 | Lee |
| 2012/0172892 A1* | 7/2012 | Grubac ............. A61N 1/3756 606/129 |
| 2012/0197373 A1 | 8/2012 | Khairkhahan et al. |
| 2012/0232565 A1 | 9/2012 | Kveen et al. |
| 2012/0271134 A1 | 10/2012 | Allan et al. |
| 2012/0330392 A1 | 12/2012 | Regnier et al. |
| 2013/0006261 A1 | 1/2013 | Lampropoulos et al. |
| 2013/0006262 A1 | 1/2013 | Lampropoulos et al. |
| 2013/0012925 A1 | 1/2013 | Berthiaume et al. |
| 2013/0035636 A1 | 2/2013 | Beasley et al. |
| 2013/0035748 A1 | 2/2013 | Bonner et al. |
| 2013/0053921 A1 | 2/2013 | Bonner et al. |
| 2013/0079798 A1 | 3/2013 | Tran et al. |
| 2013/0079861 A1 | 3/2013 | Reinert et al. |
| 2013/0103047 A1 | 4/2013 | Steingisser et al. |
| 2013/0103049 A1 | 4/2013 | Medtronic |
| 2013/0110219 A1 | 5/2013 | Bomzin et al. |
| 2013/0116740 A1 | 5/2013 | Bornzin et al. |
| 2013/0116741 A1 | 5/2013 | Bornzin et al. |
| 2013/0123875 A1 | 5/2013 | Varady et al. |
| 2013/0131591 A1 | 5/2013 | Berthiaume et al. |
| 2013/0131693 A1 | 5/2013 | Berthiaume et al. |
| 2013/0253342 A1 | 9/2013 | Griswold et al. |
| 2013/0253343 A1 | 9/2013 | Waldhauser et al. |
| 2013/0253344 A1 | 9/2013 | Griswold et al. |
| 2013/0253345 A1 | 9/2013 | Griswold et al. |
| 2013/0253346 A1 | 9/2013 | Griswold et al. |
| 2013/0253347 A1 | 9/2013 | Griswold et al. |
| 2013/0296957 A1 | 11/2013 | Tronnes |
| 2014/0058494 A1 | 2/2014 | Ostroff et al. |
| 2014/0074114 A1 | 3/2014 | Khairkhahan et al. |
| 2014/0148815 A1 | 5/2014 | Wenzel et al. |
| 2014/0180306 A1 | 6/2014 | Grubac et al. |

FOREIGN PATENT DOCUMENTS

| | | |
|---|---|---|
| EP | 779080 B1 | 5/2003 |
| JP | H02-88666 | 7/1990 |
| JP | 05245215 A | 9/1993 |
| RU | 2011151104 | 6/2013 |
| WO | 03032807 A2 | 4/2003 |
| WO | 2009039400 A1 | 3/2009 |
| WO | 2009042295 A1 | 4/2009 |
| WO | 2010131157 A1 | 11/2010 |
| WO | 2012092067 A1 | 7/2012 |
| WO | 2012092074 A1 | 7/2012 |
| WO | 2014006471 A2 | 1/2014 |

OTHER PUBLICATIONS

Spickler, et al. "Totally Self-Contained Intracardiac Pacemaker" J. Electrocardiology, vol. 3, Nos. 3 & 4, pp. 325-331 (1970).

* cited by examiner

LEADLESS CARDIAC PACING DEVICES

CROSS REFERENCE TO RELATED APPLICATIONS

This application claims priority to U.S. Provisional Application No. 61/866,799 filed on Aug. 16, 2013, the entire contents of which is hereby incorporated by reference.

TECHNICAL FIELD

The present disclosure pertains to medical devices, and methods for manufacturing medical devices. More particularly, the present disclosure pertains to leadless cardiac pacing devices.

BACKGROUND

A wide variety of medical devices have been developed for medical use, for example, cardiac use. Some of these devices include catheters, leads, pacemakers, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. An example medical device may include an implantable leadless pacing device. The implantable leadless pacing device may include a pacing capsule. The pacing capsule may include a housing. The housing may have a proximal region and a distal region. A first electrode may be disposed along the distal region. One or more anchoring members may be coupled to the distal region. The anchoring members may each include a region with a compound curve.

An implantable leadless pacing device system may include a delivery catheter having a proximal region, a distal holding section, and a lumen formed therein. A push member may be slidably disposed within the lumen. A leadless pacing device may be slidably received within the distal holding section. The leadless pacing device may include a housing having a proximal region and a distal region. A first electrode may be disposed along the distal region. A plurality of anchoring members including a first anchoring member may be coupled to the distal region. The first anchoring member may be capable of shifting between a first configuration when the leadless pacing device is disposed within the distal holding section and a second configuration when the leadless pacing device is advanced out from the distal holding section. The distal holding section may have a longitudinal axis. The first anchoring member may be arranged substantially parallel with the longitudinal axis when the first anchoring member is in the first configuration. The first anchoring member may include a region with a compound curve when the first anchoring member is in the second configuration.

Another example implantable leadless pacing device system may include a delivery catheter having a proximal region, a distal holding section, and a lumen formed therein. A push member may be slidably disposed within the lumen. A leadless pacing device may be slidably received within the distal holding section. The leadless pacing device may include a housing having a proximal region and a distal region. A first electrode may be disposed along the distal region. A plurality of anchoring members including a first anchoring member may be coupled to the distal region. The first anchoring member may be capable of shifting between a first configuration when the leadless pacing device is disposed within the distal holding section and a second configuration when the leadless pacing device is advanced out from the distal holding section. A contact section of the first anchoring member may contact an inner wall surface of the distal holding section when the first anchoring member is in the first configuration. The contact section may be positioned proximally of a distal end of the first anchoring member. The first anchoring member may include a region with a compound curve when the first anchoring member is in the second configuration.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
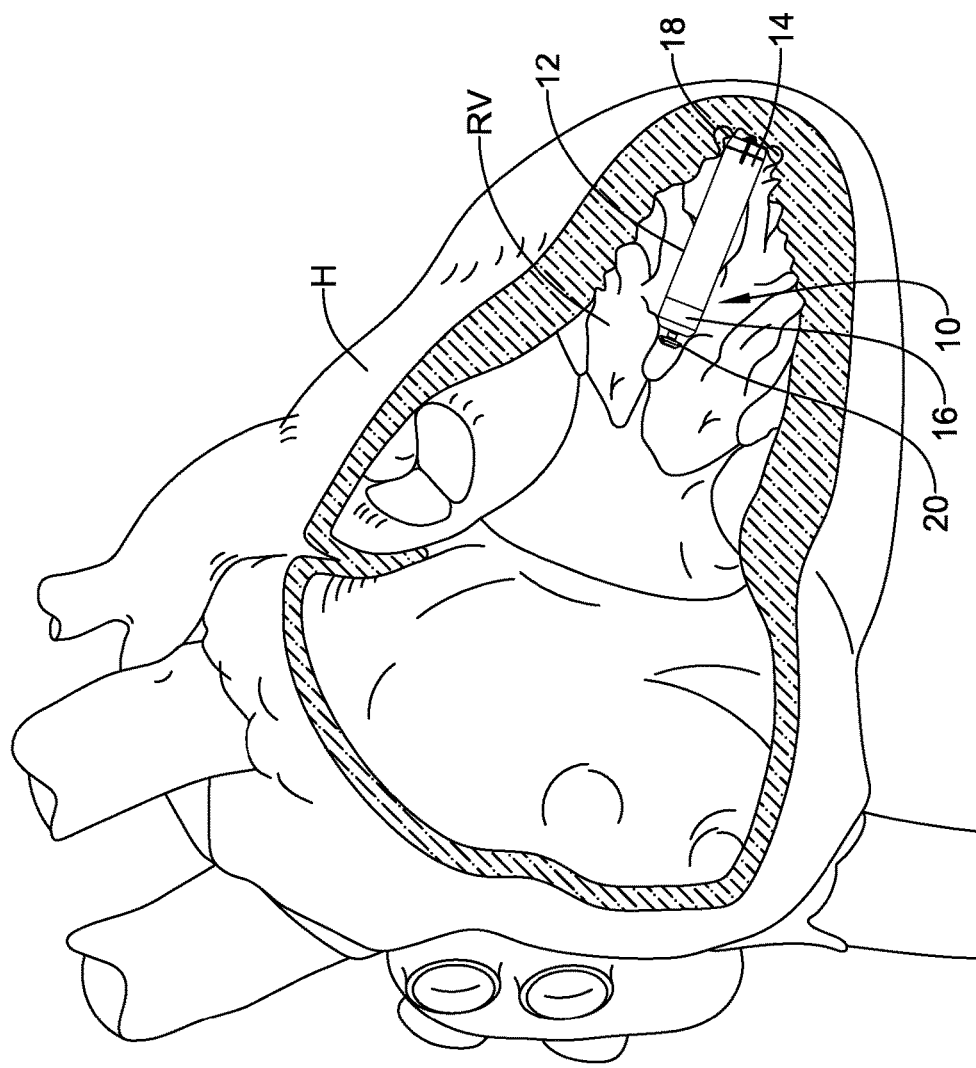
FIG. 1 is a plan view of an example leadless pacing device implanted within a heart.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

Cardiac pacemakers provide electrical stimulation to heart tissue to cause the heart to contract and thus pump blood through the vascular system. Conventional pacemakers typically include an electrical lead that extends from a pulse generator implanted subcutaneously or sub-muscularly to an electrode positioned adjacent the inside or outside wall of the cardiac chamber. As an alternative to conventional pacemakers, self-contained or leadless cardiac pacemakers have been proposed. A leadless cardiac pacemaker may take the form of a relatively small capsule that may be fixed to an intracardiac implant site in a cardiac chamber. It can be readily appreciated that the implantation of a leadless pacing device within a beating heart could become dislodged as the heart functions. Accordingly, it may be desirable for a leadless pacing device to include an anchoring mechanism and/or one or more anchoring members to help securing the pacing device to the heart.

FIG. 1 illustrates an example implantable leadless cardiac pacing device 10 implanted in a chamber of a heart H such as, for example, the right ventricle RV. Device 10 may include a shell or housing 12 having a distal region 14 and a proximal region 16. One or more anchoring members 18 may be disposed adjacent to distal region 14. Anchoring members 18 may be used to attach device 10 to a tissue wall of the heart H, or otherwise anchor implantable device 10 to the anatomy of the patient. A docking member 20 may be disposed adjacent to proximal region 16 of housing 12. Docking member 20 may be utilized to facilitate delivery and/or retrieval of implantable device 10.

Figure 2:
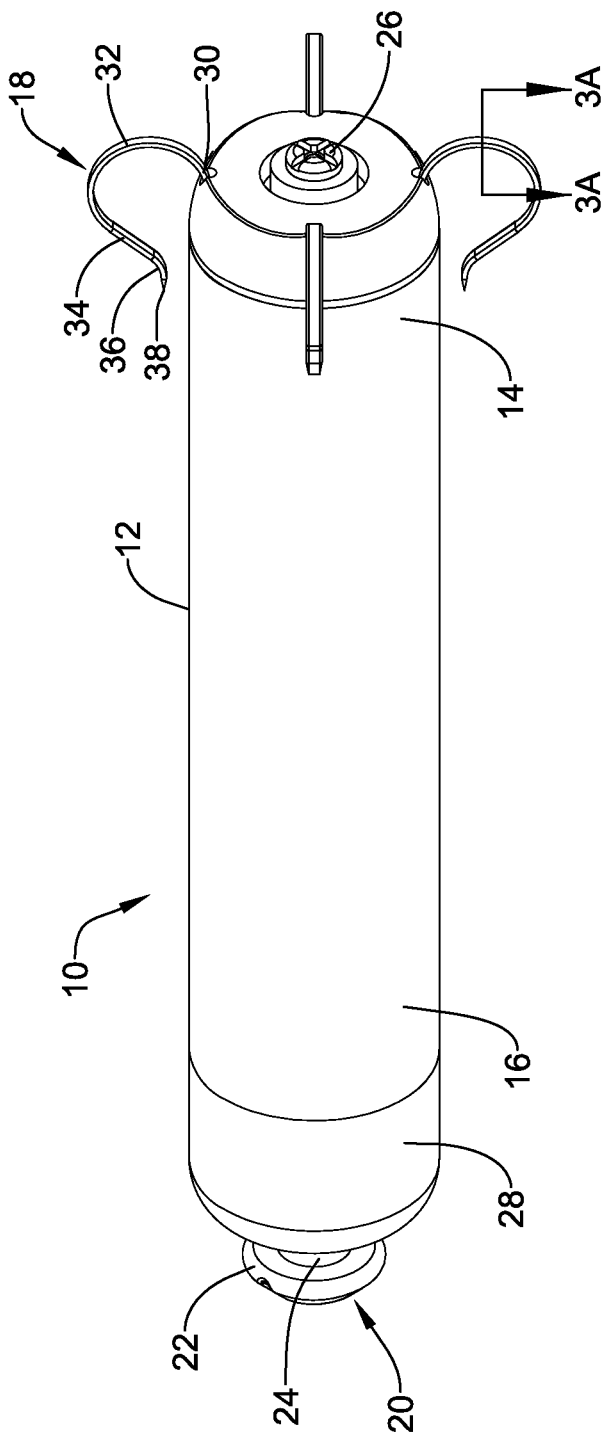
FIG. 2 is a perspective view of an example leadless pacing device.

FIG. 2 is a perspective view of device 10. Here it can be seen that docking member 20 may extend from proximal region 16 of housing 12. In at least some embodiments, docking member 20 may include a head portion 22 and a neck portion 24 extending between housing 12 and head portion 22. Head portion 22 may be capable of engaging with a delivery and/or retrieval catheter. For example, if it is desired to retrieve device 10 from the patient, a retrieval catheter may be advanced to a position adjacent to device 10. A retrieval mechanism such as a snare, tether, arm, or other suitable structure may extend from the retrieval catheter and engage head portion 22. When suitably engaged, device 10 may be pulled from the cardiac tissue and, ultimately, removed from the patient.

The implantable device 10 may include a first electrode 26 positioned adjacent to the distal region 14 of the housing 12. A second electrode 28 may also be defined along housing 12. For example, housing 12 may include a conductive material and may be insulated along a portion of its length. A section along proximal region 16 may be free of insulation so as to define second electrode 28. Electrodes 26/28 may be sensing and/or pacing electrodes to provide electro-therapy and/or sensing capabilities. First electrode 26 may be capable of being positioned against or otherwise contact the cardiac tissue of the heart H while second electrode 28 may be spaced away from the first electrode 26, and thus spaced away from the cardiac tissue.

Device 10 may also include a pulse generator (e.g., electrical circuitry) and a power source (e.g., a battery) within housing 12 to provide electrical signals to electrodes 26/28. Electrical communication between pulse generator and electrodes 26/28 may provide electrical stimulation to heart tissue and/or sense a physiological condition.

As the name suggest, anchoring members 18 may be used to anchor device 10 to the target tissue. A suitable number of anchoring members 18 may be used with device 10. For example, device 10 may include one, two, three, four, five, six, seven, eight, or more anchoring members. In at least some embodiments, anchoring members 18 may take the form of grappling hooks that are capable of piercing the cardiac tissue, looping through a portion of the cardiac tissue, and then extending back out from the cardiac tissue. In doing so, it may be desirable for anchoring members 18 to have relatively shallow penetration into the cardiac tissue. In addition, it may be desirable for anchoring members 18 to be arranged so as to be spaced from first electrode 26. Other configurations are contemplated.

In order to achieve these and other goals, anchoring members 18 may have a compound curved structure. For the purposes of this disclosure, a compound curved structure may be understood as a structure that includes a plurality of different curved regions. For example, at least some of the anchoring members 18 may include a base region 30, a first curved region 32, a generally straight region 34, a second curved region 36, and an end region 38. Base region 30 may be positioned at the junction between anchoring members 18 and housing 12. In some embodiments, base region 30 may be fixed to housing 12. In other embodiments, base region 30 may be pivotably attached to housing 12. According to these embodiments, base region 30 may have some freedom of movement relative to housing 12. In some instance, an actuation mechanism may be coupled to anchoring members 18 so that a clinician may pivot anchoring members 18 during an implantation procedure. For example, a translatable mechanical feature such as a wire, tether, or the like may be coupled to housing 12 that is capable of transmitting motion to anchoring members 18.

First curved region 32 may curve away from housing 12. In other words, the curvature of first curved region 32 may result in at least a portion of anchoring members 18 becoming positioned progressively further radially away from housing 12. For example, it may be desirable for anchoring members 18 to extend or otherwise be positioned laterally as far away from first electrode 26 as possible so as to minimize tissue irritation adjacent to where first electrode 26 contacts the wall of the heart. In addition, the curvature of first curved region 32 (and/or other regions of anchoring members 18) may be capable of secured holding device to the wall of the heart while having a relatively shallow penetration into the tissue. Shallow penetration may help to reduce local tissue irritation and/or injury of the heart wall.

In some embodiments, the radius of curvature of first curved region 32 may be constant. In other embodiments, the radius of curvature may vary along first curved region 32. For example, first curved region 32 may include a parabolic curve, hyperbolic curve, exponential curve, a curve defined by a first order polynomial, a curve defined by a second order polynomial, a curve defined by a third order polynomial, a curve defined by a fourth order or greater polynomial, etc. First curved region 32 may lie fully within a single plane (e.g., first curved region 32 may extend in only two dimension) or first curved region 32 may lie within more than one plane (e.g., first curved region 32 may extend in three dimensions). These are just examples. Other curves, shapes, configurations, etc. are contemplated.

Generally straight region 34, as the name suggests, may be substantially free from a curve. Generally straight region 34 may have a suitable length. For example, in some embodiments it may be desirable for greater separation between first curved region 32 and second curved region 36. In such embodiments, it may be desirable for generally straight region 34 to have a relatively longer length. In other embodiments, less separation may be desired between curved portions 32/36 and, thus, generally straight region 34 may be relatively short. In still other embodiments, anchoring members 18 may lack generally straight region 34. In other words, first curved region 32 may be directly attached to or otherwise continuous with second curved region 36.

Second curved region 36 may curve toward housing 12. In at least some embodiments, the curvature of second curved region 36 may be oriented in the opposite direction of first curved region 32. Just like first curved region 32, second curved region 36 may have a constant or variable radius of curvature.

End region 38 may be generally straight or end region 38 may include a curve. In at least some embodiments, end region 38 may have a point or relatively sharpened end that may be capable of penetrating tissue.

In addition to allowing device 10 to be securely anchored to the heart of a patient, anchoring members 18 may also allow for acute repositioning of device 10. For example, device 10 may be secured to the heart of a patient via anchoring members 18. If it desired to relocate device 10, a suitable retrieval and/or repositioning device may be used to engage device 10 so that it can be repositioned (e.g., removing anchoring members 18 from the tissue and moving device 10 to another desirable location) and re-anchored.

Figure 3B:
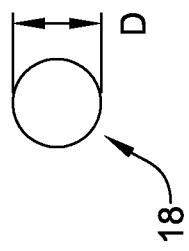
FIG. 3B is an alternative cross-sectional view.
Figure 3C:
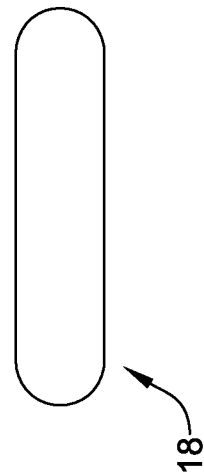
FIG. 3C is an alternative cross-sectional view.
Figure 3A:
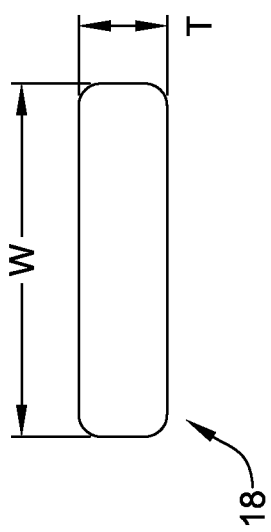
FIG. 3A is a cross-sectional view taken through line 3A-3A.

The cross-sectional shape of anchoring members 18 may vary. For example, at least some of anchoring members 18 may have a generally rectangular cross-sectional shape as shown in FIG. 3A. According to these embodiments, the width W of anchoring member 18 may be greater than the thickness T. However, in other embodiments, the thickness T may be greater than the width W. In other embodiments, at least some of anchoring members 18 may have a generally circular cross-sectional shape with a diameter D as depicted in FIG. 3B. Other cross-sectional shapes are contemplated. For example, anchoring members 18 can have an oval cross-sectional shape (e.g. as depicted in FIG. 3C), a semi-circular cross-sectional shape, a polygonal cross-sectional shape (e.g., triangular, square, quadrilateral, pentagonal, hexagonal, octagonal, etc.), combinations thereof (e.g., a polymeric shape with rounded edges or corners), or any other suitable shape. Anchoring members 18 may have the same cross-sectional shape along essentially the full length thereof. Alternatively, the cross-sectional shape may vary along the length of anchoring members 18. For example, portions of anchoring members 18 may have a generally non-circular cross-sectional shape and other portions of anchoring members 18 may have a generally circular cross-sectional shape. Furthermore, in some embodiments all of anchoring members 18 may have the same cross-sectional shape and/or profile. In other embodiments, the various anchoring members 18 of a given device 10 may differ from one another.

Figure 4:
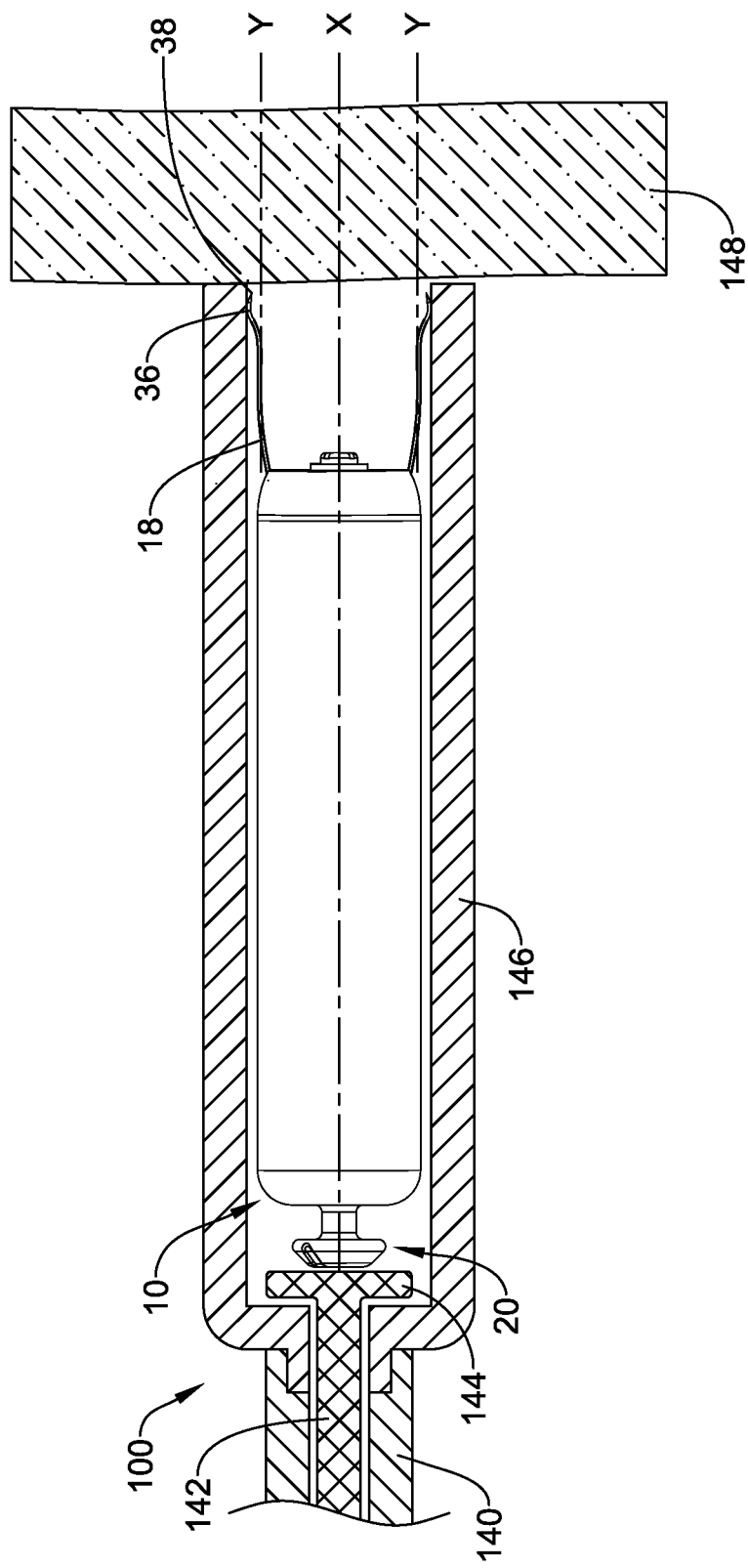
FIG. 4 is a partial cross-sectional side view of an example medical device system positioned adjacent to a cardiac tissue.

FIG. 4 illustrates a delivery catheter 100 that may be used, for example, to deliver device 10 to a suitable location within the anatomy (e.g., the heart). Catheter 100 may include a proximal member or region 140 and a distal member or holding section 146. A push member 142 may be disposed (e.g., slidably disposed) within proximal region 140. A head region 144 of push member 142 may be disposed within distal holding section 146. Head region 144 may be capable of engaging docking member 20 of device 10. Push member 142 may be used to "push" device 10 out from distal holding section 146 so as to deploy and anchor device 10 within a target region 148 (e.g., a region of the heart such as the right ventricle). Catheter 100 may be advanced through the vasculature to target region 148. For example, catheter 100 may be advanced through a femoral vein, into the inferior vena cava, into the right atrium, through the tricuspid valve, and into the right ventricle. Target region 148 may be a portion of the right ventricle. For example, target region 148 may be a portion of the right ventricle near the apex of the heart. Target region 148 could also be other regions including other regions of the heart (e.g., the right atrium, the left ventricle, the left atrium), blood vessel, or other suitable targets.

Anchoring members 18 may be capable of shifting between a first configuration and a second configuration. For example, when device 10 is disposed within distal holding section 146 of delivery catheter 100, anchoring members 18 may be in the first configuration. When so configured, anchoring members 18 may extend distally from device 10 in a generally more straightened configuration. In other words, anchoring members 18 may be oriented in the distal direction. For example, catheter 100 may have a longitudinal axis X and anchoring members 18 may corresponding longitudinal axis Y that is generally parallel with the longitudinal axis X of catheter 100. However, anchoring members 18 need not extend exactly parallel with the longitudinal axis X of catheter 100 and, instead, may be generally oriented in the distal direction.

Figure 5:
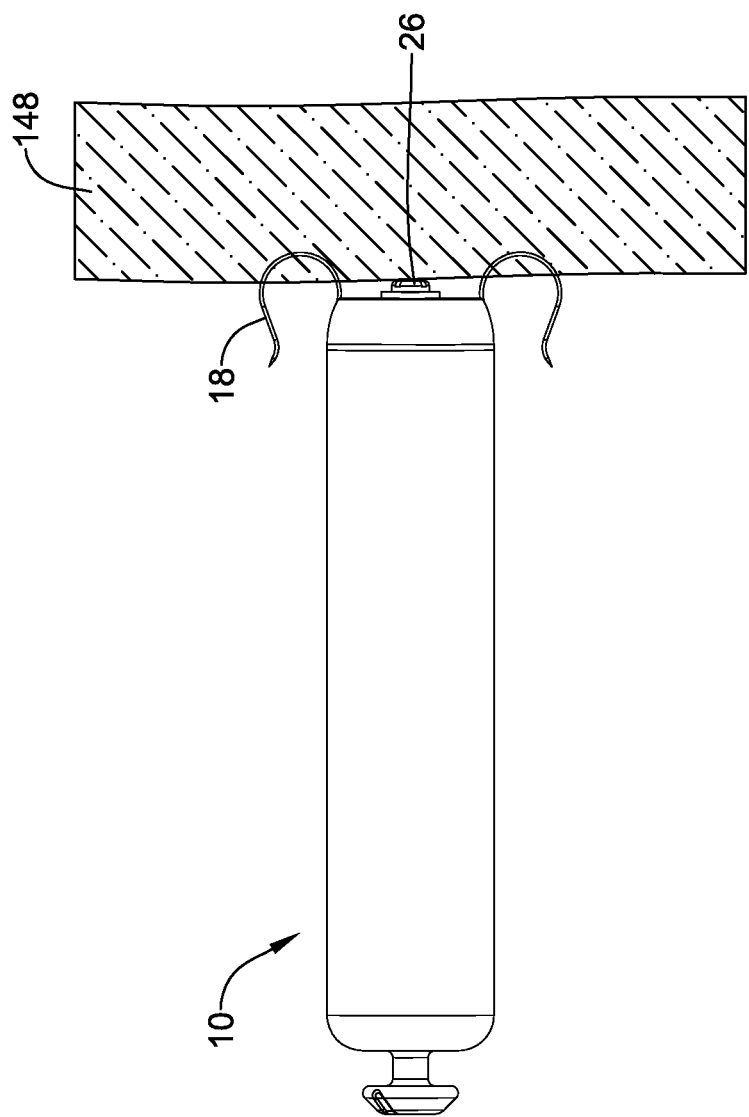
FIG. 5 is a partial cross-sectional side view of an example leadless pacing device attached to a cardiac tissue.

When device 10 is suitably positioned adjacent to target region 148, push member 142 may be distally advanced to push device 10 distally so that anchoring members 18 engage target region 148. In doing so, anchoring members may shift to the second configuration as shown in FIG. 5. When in the second configuration, anchoring members 18 may have the compound curved configuration. The compound curve of anchoring members 18 may help to guide anchoring members 18 away laterally away from the tissue entry point and then back out of the tissue at a location that is laterally spaced from the entry point.

In at least some embodiments, anchoring members 18 may still maintain a compound curvature (e.g., albeit in an altered shape) when in the more straightened configuration. For example, when device 10 is disposed within a delivery catheter, anchoring members 18 may still maintain the compound curve. In other embodiments, one or more of curves formed in anchoring members 18 may be substantially straightened such that anchoring members 18 may be considered as no longer having a compound curve when in the more straightened configuration. When shifting to the second configuration (e.g., which may be considered a deployed, implanted, delivered, or "unbiased" configuration), anchoring members 18 may have or otherwise return to a shape that includes the compound curve.

Figure 6:
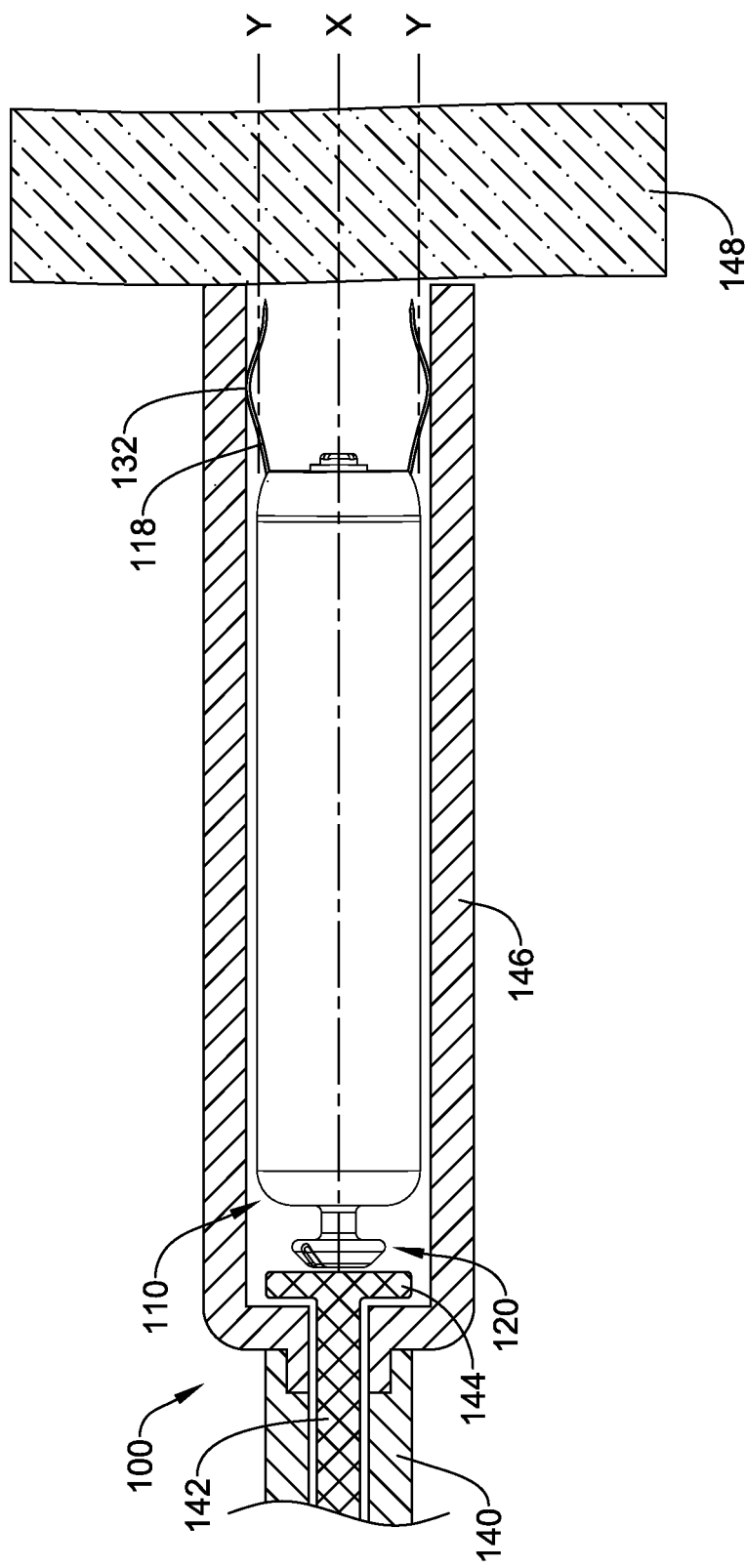
FIG. 6 is a partial cross-sectional side view of another example medical device system positioned adjacent to a cardiac tissue.

When in the first configuration, a portion of anchoring members 18 may engage an inner wall surface of distal holding section 146. The portion of anchoring member 18 that engages the inner wall surface of distal holding section 146 may be positioned proximally of the distal end of anchoring member 18. For example, second curved region 36 may engage the inner wall surface of distal holding section 146 as shown in FIG. 4. Other arrangements are contemplated. For example, FIG. 6 illustrates device 110 (which may be similar in form and function to other devices disclosed herein) including anchoring member 118 and docking member 120. Here it can be seen that first curved region 132 may engage the inner wall surface of distal holding section 146.

Figure 7:
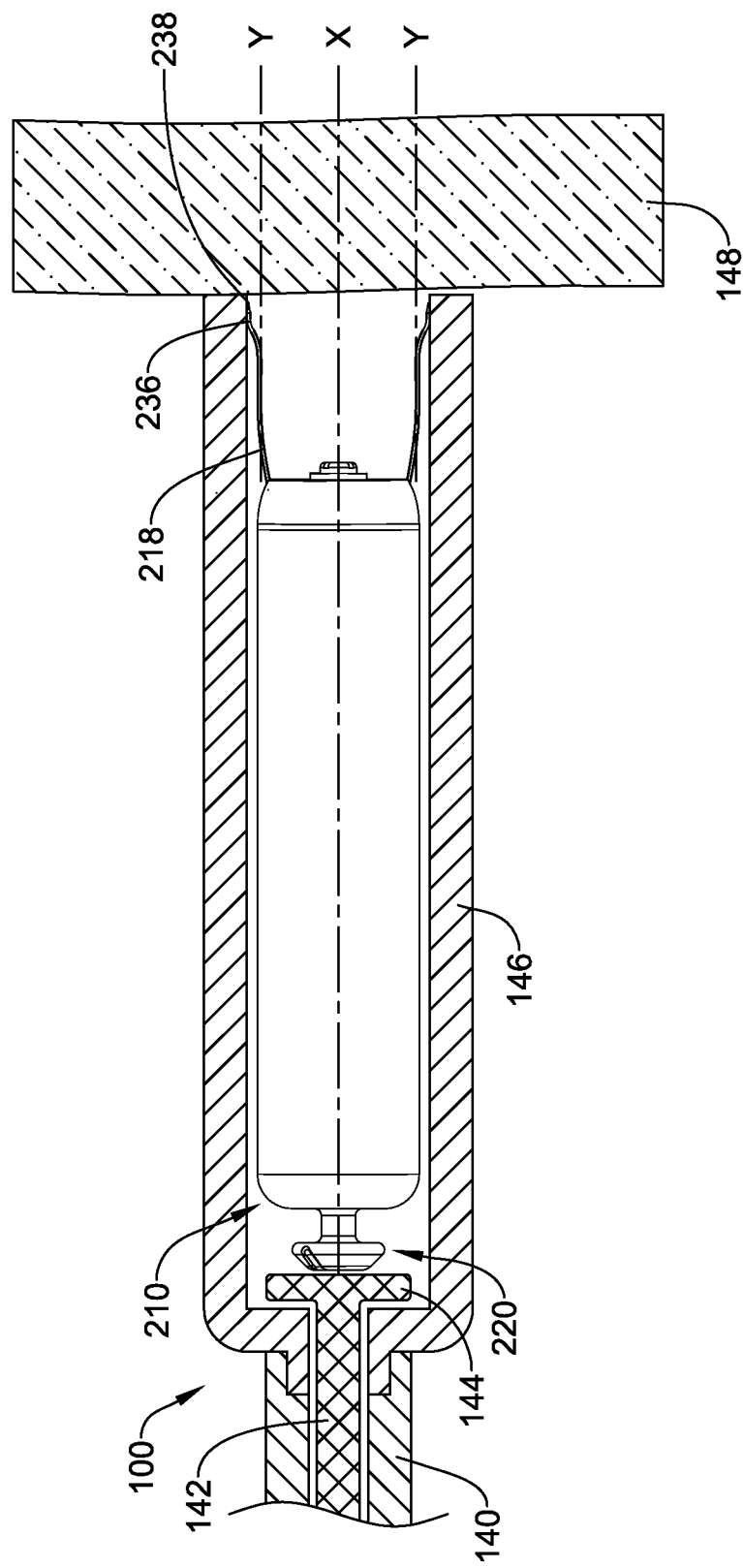
FIG. 7 is a partial cross-sectional side view of another example medical device system positioned adjacent to a cardiac tissue.

FIG. 7 illustrates device 210 (which may be similar in form and function to other devices disclosed herein) including anchoring member 218 and docking member 220. In this embodiment, a section of anchoring member 218 extending from second curved region 232 to tip 238 may lie flat against the inner wall surface of distal holding section 146.

The materials that can be used for the various components of device 10 and catheter 100 (and/or other devices/catheters disclosed herein) may include those commonly associated with medical devices. For example, device 10 and/or catheter 100 may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of device 10 and/or catheter 100 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of device 10 and/or catheter 100 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of device 10 and/or catheter 100 to achieve the same result.

In some embodiments, a degree of Magnetic Resonance Imaging (MRI) compatibility is imparted into device 10 and/or catheter 100. For example, device 10 and/or catheter 100 (or portions thereof) may be made of a material that does not substantially distort the image and create substantial artifacts (i.e., gaps in the image). Certain ferromagnetic materials, for example, may not be suitable because they may create artifacts in an MRI image. Device 10 and/or catheter 100 (or portions thereof) may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. An implantable leadless pacing device, comprising:
    a pacing capsule including a housing, the housing having a proximal region and a distal region;
    a first electrode disposed along the distal region; and
    a plurality of anchoring members coupled to the distal region,
    wherein each of the anchoring members is capable of shifting between a first, delivery configuration when positioned within a holding region of a delivery catheter, and a second, deployed configuration when deployed therefrom, the anchoring members each including a region with a compound curve when in the deployed configuration, wherein the region with the compound curve includes a first curved section and a second curved section, wherein each anchoring member extends between a base region connected to the housing and a free end, wherein each anchoring member has first and second outer surfaces on opposite sides of the anchoring member, the first and second outer surfaces each extending between the base region and the free end, wherein the first outer surface is convex in the first curved section and concave in the second curved section, wherein the free end of each of the anchoring members includes a sharpened tip that points in a proximal direction when in the deployed configuration, and wherein each of the anchoring members includes an outermost surface proximal of the tip that is positioned radially outward of the sharpened tip in the delivery configuration.

2. The implantable leadless pacing device of claim 1, wherein the first curved section is oriented in a first direction and wherein the second curved section is oriented in a second direction different from the first direction.

3. The implantable leadless pacing device of claim 2, wherein the first direction is opposite the second direction.

4. The implantable leadless pacing device of claim 1, wherein the first curved section, the second curved section or both are capable of causing the anchoring members to move laterally away from the first electrode when the anchoring members extend within a target tissue.

5. The implantable leadless pacing device of claim 1, wherein the first curved section, the second curved section or both have a radius of curvature that varies.

6. The implantable leadless pacing device of claim 1, wherein the second outer surface is concave in the first curved section and convex in the second curved section.

7. The implantable leadless pacing device of claim 1, wherein the second curved section includes a curve extending away from the housing and up to the free end.

8. An implantable leadless pacing device system, the system comprising:
    a delivery catheter having a proximal section, a distal holding section, and a lumen formed therein;
    a push member slidably disposed within the lumen;
    a leadless pacing device slidably received within the distal holding section, the leadless pacing device comprising:
        a pacing capsule including a housing, the housing having a proximal region and a distal region,
        a first electrode disposed along the distal region, and
        a plurality of anchoring members coupled to the distal region, each anchoring member including first and second outer surfaces on opposite sides of the anchoring member;
    wherein each of the anchoring members is capable of shifting between a first configuration when the leadless pacing device is disposed within the distal holding section and a second, deployed configuration when the leadless pacing device is advanced out from the distal holding section;

wherein the distal holding section has a longitudinal axis;

wherein each of the anchoring members is arranged substantially parallel with the longitudinal axis when the anchoring members are in the first configuration with the first outer surface contacting an inner wall surface of the distal holding section while spacing a distal sharpened tip away from the inner wall surface of the distal holding section; and wherein each of the anchoring members includes a region with a compound curve when the anchoring members are in the deployed configuration, wherein each anchoring member has a length extending between a base region and a free end, the base region connecting the anchoring member to the housing, wherein the region with the compound curve includes a first curved section proximate the base region and a second curved section proximate the free end, wherein the first outer surface is concave in the first curved section and convex in the second curved section in the deployed configuration, wherein the second outer surface is convex in the first curved section and concave in the second curved section in the deployed configuration, and wherein the free end of each of the anchoring members includes the distal sharpened tip that points in a proximal direction when in the deployed configuration.

9. The system of claim 8, wherein the first curved section is oriented in a first direction and wherein the second curved section is oriented in a second direction different from the first direction.

10. The system of claim 9, wherein the first direction is opposite the second direction.

11. The system of claim 8, wherein a contact section of each of the anchoring members contacts an inner wall surface of the distal holding section when the anchoring members are in the first configuration.

12. The system of claim 8, wherein a contact section of each anchoring member located proximal of the free end of the anchoring member contacts the inner wall surface of the distal holding section when the anchoring members are in the first configuration.

13. The system of claim 12, wherein the contact section of each anchoring member extends between the free end of the anchoring member and a point disposed proximal of the free end.

14. The system of claim 8, wherein the first curved section, the second curved section or both of each anchoring member are capable of causing the anchoring member to move laterally away from the first electrode when the anchoring member extends within a cardiac tissue.

15. An implantable leadless pacing device system, the system comprising:
 a delivery catheter having a proximal section, a distal holding section, and a lumen formed therein;
 a push member slidably disposed within the lumen;
 a leadless pacing device slidably received within the distal holding section, the leadless pacing device comprising:
  a pacing capsule including a housing, the housing having a proximal region and a distal region,
  a first electrode disposed along the distal region, and
  a plurality of anchoring members coupled to the distal region;
 wherein each of the anchoring members is capable of shifting between a first configuration when the leadless pacing device is disposed within the distal holding section and a second, deployed configuration when the leadless pacing device is advanced out from the distal holding section such that a free end of each of the anchoring members includes a distal tip that points in a proximal direction when in the deployed configuration;
 wherein a contact section of each of the anchoring members contacts an inner wall surface of the distal holding section when the anchoring member is in the first configuration;
 wherein the contact section of each of the anchoring members is positioned proximally of the distal tip of the anchoring member;
 wherein the distal tip of each of the anchoring members is spaced away from the inner wall surface of the distal holding section in a radial direction when the anchoring member is in the first configuration;
 wherein each of the anchoring members extends between a base region connected to the housing and the free end, wherein each anchoring member has first and second outer surfaces on opposite sides of the anchoring member, the first and second outer surfaces each extending between the base region and the free end, wherein each anchoring member includes a region with a compound curve when the anchoring members are in the deployed configuration;
 wherein the region with the compound curve includes a first curved section and a second curved section located between the first curved section and the distal tip, wherein the contact section of each of the anchoring members includes a curved portion of the second curved section, wherein the first outer surface along the contact section contacts an inner surface of the distal holding section in the first configuration, wherein the first outer surface is convex through the curved portion when in the deployed configuration and in the first configuration, and wherein the second outer surface is concave through the curved portion when in the deployed configuration and in the first configuration.

16. The system of claim 15, wherein the second curved section curves away from the housing toward the distal tip of the anchoring member when in the deployed configuration.

17. The system of claim 16, wherein the distal tip is a sharpened distal tip.

18. The system of claim 15, wherein the first outer surface is concave in the first curved section and convex in the second curved section, and wherein the second outer surface is convex in the first curved section and concave in the second curved section.

19. The system of claim 15, wherein the first outer surface is convex distal of the contact section to the distal tip in the deployed configuration and in the first configuration, and the second outer surface is concave distal of the contact section to the distal tip in the deployed configuration and in the first configuration.

* * * * *